United States Patent
Lontine et al.

Patent Number: 6,139,547
Date of Patent: Oct. 31, 2000

[54] PARTIALLY COATED ELECTRODES, MANUFACTURE AND USE

[75] Inventors: Michael D. Lontine, Westminster; Gene Arts, Berthoud, both of Colo.

[73] Assignee: Sherwood Services AG, Shaffhausen, Switzerland

[21] Appl. No.: 08/934,688

[22] Filed: Aug. 22, 1997

Related U.S. Application Data

[63] Continuation of application No. 08/367,493, Dec. 30, 1994, Pat. No. 5,713,895.

[51] Int. Cl.$^7$ ..................................................... A61B 17/36
[52] U.S. Cl. .................................. 606/41; 606/45; 606/49
[58] Field of Search ................................ 606/41–50, 32, 606/35; 607/152

[56] References Cited

U.S. PATENT DOCUMENTS 5,406,945   4/1995   Riazzi et al. ............................. 607/152

*Primary Examiner*—Linda C. M. Dvorak
*Assistant Examiner*—David M. Ruddy

[57] ABSTRACT

A partially coated electrosurgical electrode has a portion of a medical grade metallic material as a substrate for energy application. Conductive of sites of metallic material or alloys thereof pass energy through peaks that define valleys nearby. A partial coating in the valleys has a low surface free energy. A treated surface across the peaks and generally over the filled valleys is relatively smooth for non stick characteristics during application of electrosurgery to tissue and bodily fluids. Openings in the treated surface through the partial coating are at the peaks of conductive sites to expose the metallic material or alloys thereof. The partial coating is a fluorinated polymer. The treated surface is a relatively even level that is not flat. The metallic material substrate is an alloy of stainless steel or nickel chrome. A mechanically deformed surface finish, plasma or vapor deposition on the substrate forms the conductive sites. A method of manufacturing the electrode has steps including preparing it the metallic conductor, making it with the conductive material having peaks above the valleys as conductive sites, applying the partial coating to it and treating the surface across the peaks and generally over the filled valleys of the partially coated electrically conductive electrode. Locating the openings among the valleys is a step. Treating may be mass finishing, such as vibratory or tumbling the partially coated electrodes with or without abrasive material media or polishing, buffing, surface grinding, abrasive belt grinding or sanding with abrasive material. Making the peaks and valleys can be by stamping, coining, burnishing, embossing, threading, tumbling, vibrating, shot peening, wire brushing, grit blasting, thermal spraying, with powder, with wire supplied to melt and be distributed, or with high velocity oxygen fuel and a nickel, cobalt alloy, stainless steel or a nickel chrome alloy. A manufacturing method for the electrode has coating a strip of metal with the low surface energy polymer and forming it in a stamping operation with a raw edge metal edge.

9 Claims, 3 Drawing Sheets

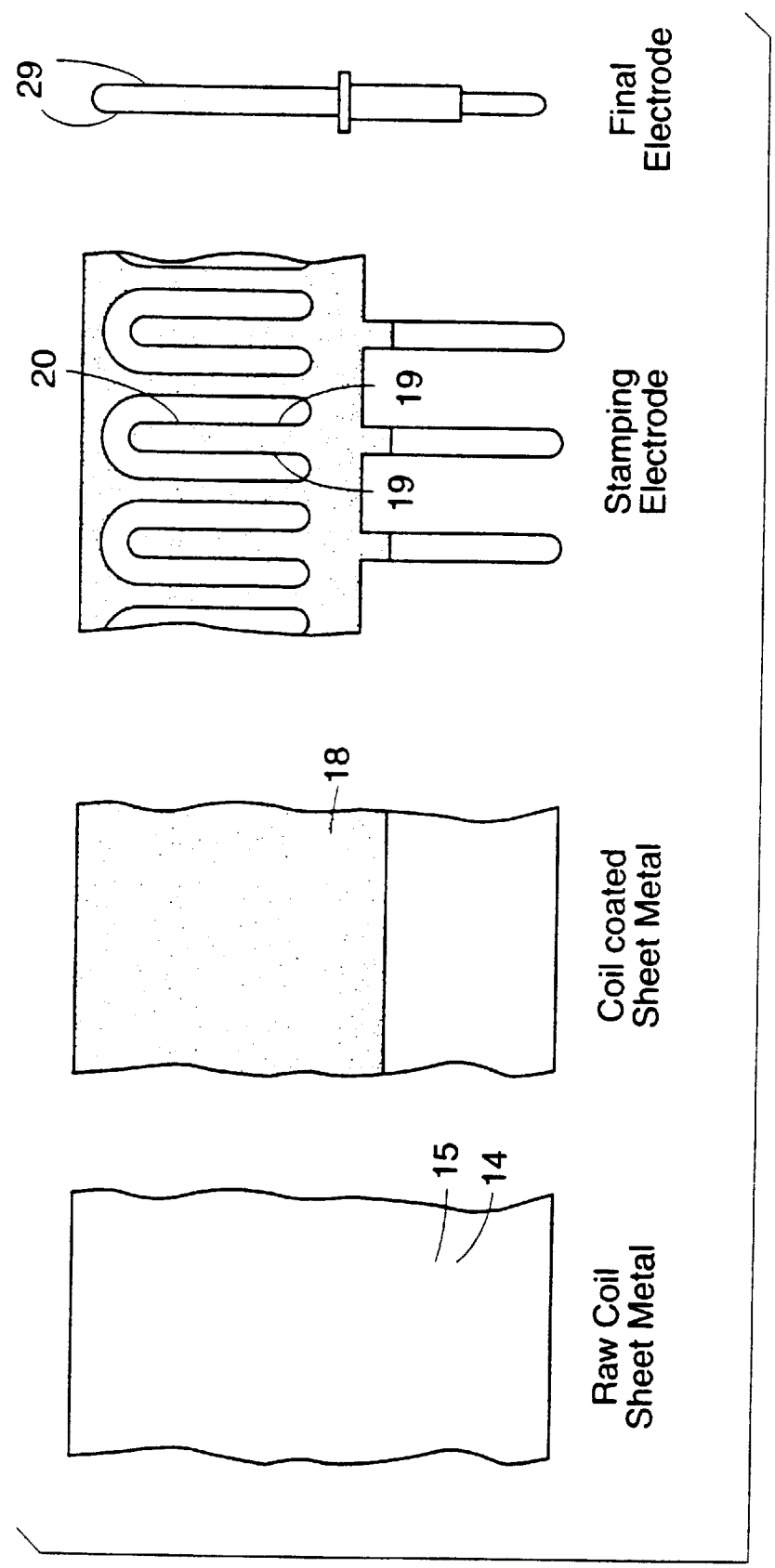

PARTIALLY COATED ELECTRODES, MANUFACTURE AND USE

This is a continuation of application Ser. No. 08/367,493, filed on Dec. 30, 1994, now U.S. Pat. No. 5,713,895.

FIELD OF THE INVENTION

This relates to partially coated electrosurgical electrodes for the application of electromagnetic energy to tissue of animal and human and more particularly to the cleanability of such tips.

BACKGROUND OF THE DISCLOSURE

Tips for electrosurgical use are subject to high temperature at least whereat the electrosurgical arc emanates during, e. g. fulguration or coagulation. The heat thus provided by ohmic coupling through air causes the proteins in the bodily fluids to coagulate and adhere to the tips.

Coatings have been used to increase the ease of cleanability of the electrosurgical tips. U.S. Pat. No. 4,785,807 has a primer and top coating of Teflon polymer over an etched or abraded stainless steel tip. The coating is thin and during application of electromagnetic energy it is said that there is capacitive coupling to allow passage of power to the tissue being treated. Thus, the Teflon polymer surface should remain largely intact and so the cleanability of the tip is good.

U.S. Pat. No. 4,492,231 discusses temperature, tip conductivity and sticking of desiccated blood in a bipolar forceps.

U.S. Pat. Nos. 4,232,676 and 4,314,559 assigned to Corning Glass Works, disclose mechanically cutting knives or scalpel tips that have areas for electrocautery and other areas which do not conduct high frequency power. The '676 patent has bipolar electrodes on the same tip so that power passing therebetween will cauterize bleeders thereagainst. The '559 patent is an electrically conductive coating over a glass scalpel to which a silver brazing paste has been applied forming a surface finish having interstices to be filled with Teflon polymer for providing non-stick properties. Alternately, platinum is applied with a rough and Teflon polymer filled surface. Only portions of the scalpel that are covered have an electrical connection between them and the tissue; the silver or platinum conductors have numerous problems. Most importantly, these noble metals are expensive and applied in a relative thin layer which must be mechanically compatible with the electrosurgical blade or tip. In use the surgeon may flex the blade during cleaning as for example, while wiping the used tip on a cleaning pad, patient drape or the like. Good mechanical connection between the conductive layer and the glass substrate is essential to prevent fracture of the coating or still worse flaking of the coating into the wound. The glass substrate is not a deformable material and would fracture under bending and therefore be unacceptable for use in surgery. In addition, biocompatability of the conductive layer and the tissue is critical to a commercial product and silver is not an endorsed material for contact with a wound. No commercially viable method of making is taught in '559. Consequently, a conductive layer that is metallurgically, mechanically and electrically compatible and biocompatable has not been known. The platinum conductive layer in the '559 patent was found to adhere poorly, be expensive and therefore unacceptable.

The Teflon polymer fills interstices, inclusions and the like at the surface providing non-stick areas on the cutting, cauterizing or coagulating instrument. The '559 patent teaches of a surface which provides areas of Teflon polymer and raw metal and so recognizes the conductive nature of the tip and permits energy flow without capacitive coupling or the need to overcome the electrical insulative properties of the polymer coating. Specifically, interstices along the conductive layer on the substrate of the metal tip are filled with primer and a top coat of Teflon polymer. The surface is thus partly conductive metal and partly cleanable Teflon polymer but the problems of compatibility with known conductive layer materials have hampered commercially successful blades.

Cookware has been made with filled fluoropolymer to reinforce the relatively soft polymer against scrapes and abrasions. In particular, fillers such as mica and other minerals, metals, ceramics and other materials have been used for that purpose and to improve the appearance of the coated cookware. There is no electrosurgical energy conducted in cookware. No partially coated electrosurgical electrodes exist wherein an easily cleaned electrosurgical electrode having a partial coating of fluorinated polymer including areas of exposed and compatible metallic conductor therethrough and uniformly distributed thereabout for providing an effective conductive and cleanable electrode are known in the prior patents. It has been found that the cleanability of the electrosurgical tips is a function of surface finish as well as the surface free energy of the partial coating. The burning through the fully coated electrosurgical electrodes has been a problem which is corrected by the partially coated electrode disclosed and claimed herein. Significant reductions of adherence of coagulum to the electrosurgical electrode is possible with the partially coated blade.

SUMMARY OF THE INVENTION

A partially coated electrosurgical electrode preferably applies electromagnetic energy in either a monopolar or a bipolar circuit to and through the tissue and the bodily fluids of an animal or human. The partially coated electrosurgical electrode may have an electrically conductive electrode for connection to a source of electromagnetic electrosurgical energy and for transmission of the electromagnetic electrosurgical energy in the circuit to and through the tissue and the bodily fluids of the animal or human. A portion of the electrically conductive electrode is most preferably a medical grade biocompatable metallic material as a substrate thereof. The portion can be located for the application of electromagnetic energy in either a monopolar or a bipolar circuit to and through the tissue and the bodily fluids of an animal or human. Conductive sites preferably pass electrosurgical energy located on the portion of the medical grade biocompatable metallic material substrate. The conductive sites may include peaks defining valleys thereby. The conductive sites are preferably formed of the medical grade biocompatable metallic material substrate or alloys thereof. A partial coating may reside primarily in the valleys disposed for contact with the tissue and the bodily fluids of the animal or human during electrosurgical application of the partially coated electrosurgical electrode. The partial coating could have a low surface free energy. A treated surface is preferably substantially across the peaks and generally over the filled valleys of the partially coated electrically conductive electrode. The treated surface might be relatively smooth for non stick mechanical characteristics during application of electrosurgical effects to tissue and bodily fluids. Openings are most preferably in the treated surface through the partial coating. The openings formed in the treated surface might be substantially at the peaks of conductive sites thereby exposing the medical grade biocompatable metallic material or alloys thereof. The openings are most preferably located primarily about and among the valleys filled with the partial coating so that the smooth treated surface formed of the openings and the filled valleys permits the direct passage of electromagnetic electrosurgical energy by conduction of electrons through the circuit between the openings therein and the tissue and the bodily fluids. It is preferred that, the filled valleys can provide the partial coating having an easily cleaned low surface free energy.

The partial coating is preferably a fluorinated polymer making direct passage of electrosurgical energy impossible without a breakdown of the dielectric properties of the fluorinated polymer. The fluorinated polymer may be conductive. The conductive sites are in the preferred embodiment carried on the substrate and electrical couple to transmit electrosurgical energy. The treated surface can be reduced to a relatively even level that is not flat whereon the openings and the filled valleys of partial coating form a generally undulating surface for reducing mechanical coupling of coagulum for lowering the surface free energy thereacross while increasing the size of the openings relative to the peaks. The openings are preferred to be in the range of about three to 20 percent of the area of the portion of the electrically conductive electrode having a medical grade biocompatable metallic material as a substrate thereof. The treated surface might have peaks reduced to nearly the level of the filled valleys.

The medical grade biocompatable metallic material substrate may be substantially an alloy of stainless steel. The medical grade biocompatable metallic material substrate could be primarily an iron nickel chrome alloy. The conductive sites might be formed as a plasma deposition of the conductive material as the substrate. A mechanically deformed surface finish on the medical grade biocompatable metallic material electrically conductive electrode substrate could be used to produce the peaks and valleys of the conductive sites. A vapor deposition of the medical grade biocompatable metal can form the conductive sites on the medical grade biocompatable metallic material electrically conductive electrode substrate as the peaks. The partial coating might include a solid lubricant compounded to the fluorinated polymer. The partial coating need only be a low surface energy polymer. The medical grade biocompatable metallic material conductive sites might have a high nickel content at the openings.

A method of manufacturing a partially coated electrosurgical electrode for the application of electromagnetic energy in either a monopolar or a bipolar circuit through the tissue and the bodily fluids of an animal or human can include steps. Preparing an electrically conductive electrode of a medical grade biocompatable metallic material substrate for connection to a source of electromagnetic electrosurgical energy at one end thereof and for transmission of the electromagnetic electrosurgical energy in the circuit from another end thereof to and through the tissue and the bodily fluids of the animal or human may be a step. Making the electrically conductive electrode about its one end with an electrically conductive material for the conductive sites which are the conductive material preferably the same medical grade biocompatable metal of the substrate, the making of the electrically conductive electrode to have peaks in the range of about 1 to 50 microns in height above the valleys for forming conductive sites for passing electrosurgical energy through the openings at the peaks and located on the one end of the electrically conductive electrode can be another step. Applying a partial coating for residing primarily in the valleys disposed for contact with the tissue and the bodily fluids of the animal or human during electrosurgical application of the partially coated electrosurgical electrode could be a further step. Applying the partial coating to a thickness in the range of about 5 to 100 microns might be another step.

The step of making may be performed by coining the one end. The step of making could be performed by burnishing the one end. The step of making can be performed by stamping the one end. The step of making might be performed by embossing the one end. The step of making can be performed by threading the one end. The step of making may preferably be performed by etching the one end. The step of making is in a preferred method performed by knurling the one end. The step of making could be performed by shot peening the one end. The step of making might be performed by wire brushing the one end. The step of making can be performed by grit blasting the one end. The step of making may preferably be performed by thermal spraying the one end with a conductive material. The step of making can preferably be performed by plasma spraying the one end with conductive powder material. The step of making is in another method performed by electric arc spraying the one end with conductive wire material. The step of making may be performed by high velocity oxygen fuel (HVOF) combustion spraying the one end with a conductive material.

Treating a surface substantially across the peaks and generally over the filled valleys of the partially coated electrically conductive electrode can be used as a step for generating relatively smooth non stick surface of a relatively uniform level so that the height of the partial coating and the peaks are reduced. Forming openings in the treated surface through the partial coating at the peaks for exposing the electrically conductive material might be another step. Locating the openings primarily among the valleys filled with the partial coating so that the smooth treated surface formed of the openings and the filled valleys could permit the direct passage of electromagnetic electrosurgical energy through the circuit between the openings therein and the tissue and the bodily fluids while the filled valleys provide the partial coating having an easily cleaned low surface free energy may be an additional step.

The step of treating may be performed by tumbling a plurality of partially coated electrodes with abrasive material media. The step of treating could be performed by tumbling a plurality of the partially coated electrodes together. The step of treating might be performed by vibrating in a container a plurality of the partially coated electrode with abrasive material media. The step of treating can be performed by vibrating in a container a plurality of the partially coated electrodes together. The step of treating is in one method preferably performed by polishing or buffing the partially coated electrode with abrasive material. The step of treating may be performed by buffing the partially coated electrode with abrasive material. The step of treating could be performed by abrasive belt grinding or sanding the partially coated electrode with abrasive material. The step of treating might be performed by surface grinding the partially coated electrode with abrasive material.

A method of manufacturing a partially coated electrosurgical electrode may have steps including coating a portion of a strip of medical grade sheet metal with a low surface energy polymer and forming electrosurgical electrodes in a progressive stamping operation including severing through the coated portion to produce at least a raw edge metal edge for electrosurgery. The step of coating the portion of the electrosurgical electrode with conductive material having peaks and valleys prior to the step of coating the strip of medical grade sheet metal with a low surface free energy polymer.

BRIEF DESCRIPTION OF THE DRAWINGS

FIG. 4 is a schematic illustration showing the relevant part of the progression for producing a partially coated electrode from a sheet metal strip that has a conductive material and thereafter covered with a low surface free energy coating that is treated.

DETAILED DESCRIPTION OF THE INVENTION

Figure 1:
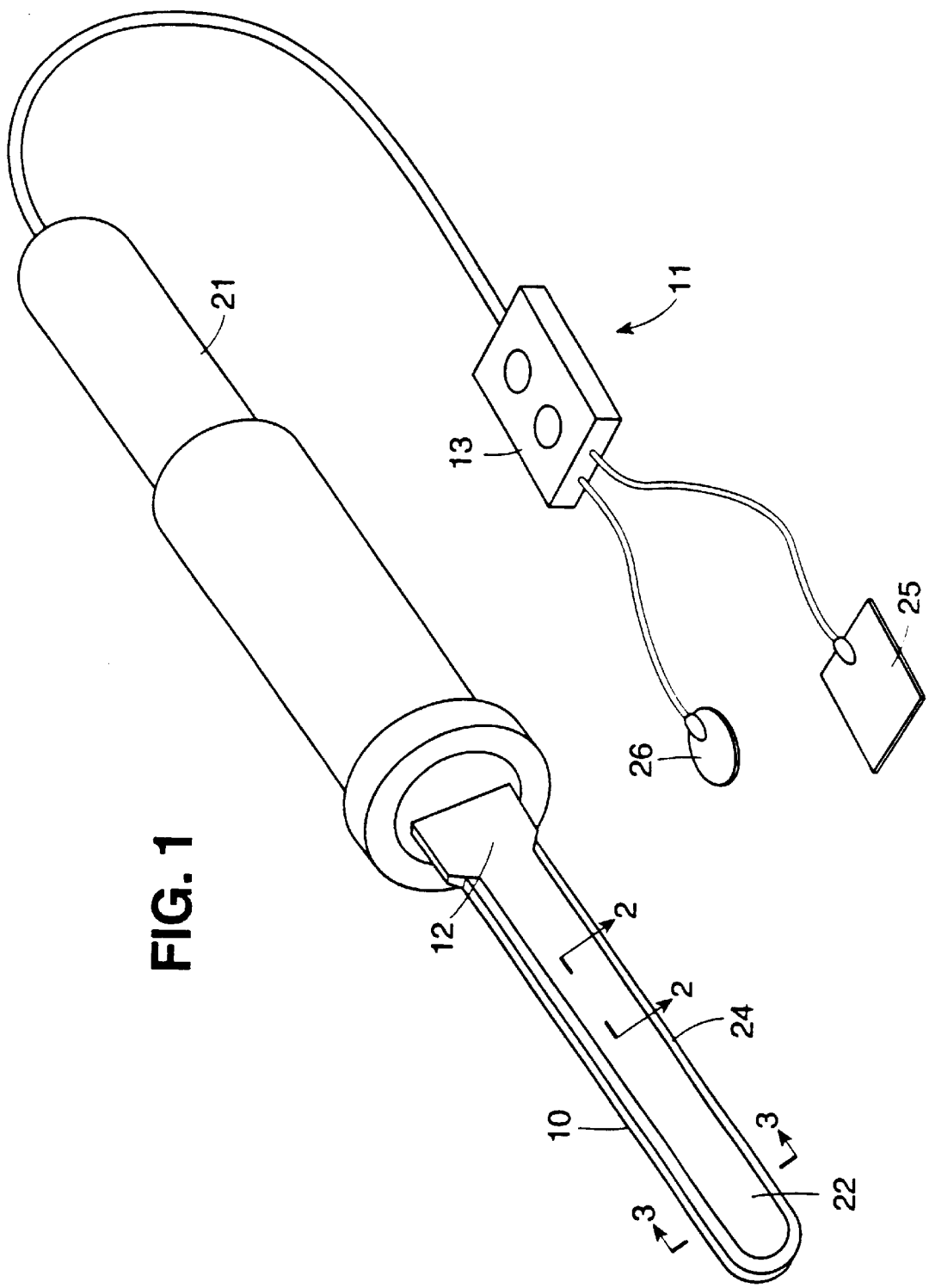
FIG. 1 is a partially coated electrosurgical electrode for the application of electromagnetic energy in either a monopolar or a bipolar circuit shown schematically and in perspective.

In FIG. 1 is a partially coated electrosurgical electrode 10 for the application of electromagnetic energy in either a monopolar or a bipolar circuit 11 and is shown schematically in perspective and in the alternative. An electrically conductive electrode 12 connects to a source of electromagnetic electrosurgical energy 13 for transmission of the electromagnetic electrosurgical energy to the tissue and the bodily fluids of the animal or human, see FIG. 1. The partially coated electrosurgical electrode 10 applies electromagnetic energy during electrosurgery in either a monopolar or a bipolar circuit 11 to and through the tissue and the bodily fluids of an animal or human. A portion of the electrically conductive electrode 12 is a medical grade biocompatable metallic material as a substrate 14 thereof, as in FIGS. 2 and 3. The preferred material is stainless steel and alloys thereof but nickel and other highly conductive metals have been found to work well in electrosurgical applications.

Conductive sites 15 located on the portion of the medical grade biocompatable metallic material substrate 14 pass electrosurgical energy. The conductive sites 15 include peaks 16 defining valleys 17 thereby, as in FIG. 2 only. Consequently, the conductive sites 15 are formed of the medical grade biocompatable metallic material substrate 14 or alloys thereof. A partial coating 18 is applied to reside primarily in the valleys 17 disposed for contact with the tissue and the bodily fluids of the animal or human during electrosurgical application of the partially coated electrosurgical electrode 10. The partial coating 18 has a low surface free energy to resist sticking of coagulated tissue and bodily fluids. A treated surface 19 is substantially across the peaks 16 and generally over the filled valleys 17 of the partially coated electrically conductive electrode 10. The treated surface 19 is relatively smooth for non stick mechanical characteristics and easy cleaning on a drape, gauze or other convenient cleaning surface in the sterile field. That is to say that, there are no rough areas or edges on the treated surface for tissue or bodily fluid to coagulate to or adhere at. Openings 20 are in the treated surface 19 through the partial coating 18. In particular, the openings 20 formed in the treated surface 19 are substantially at the peaks 16 of conductive sites 15 thereby exposing the medical grade biocompatable metallic material or alloys thereof. The openings 20 are located primarily about and among the valleys 17 filled with the partial coating 18 so that the smooth treated surface 19 formed of the openings 20 and the filled valleys 17 permits the direct passage of electromagnetic electrosurgical energy by conduction of electrons through the circuit 11 between the openings 20 therein and the tissue and the bodily fluids.

Figure 2:
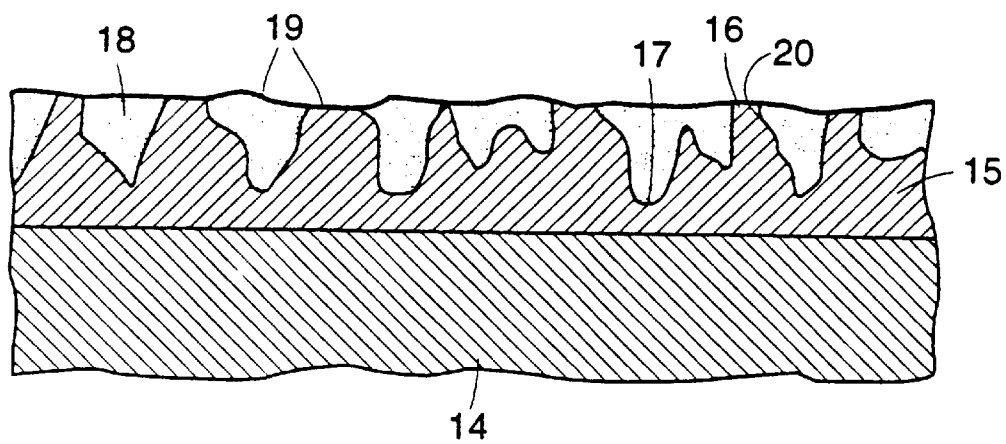
FIG. 2 is a side view in cross section as taken along lines 2—2 of FIG. 1 of the preferred embodiment of a partially coated electrosurgical electrode.

It is preferred that, the filled valleys 17 provide the partial coating 18 having an easily cleaned low surface free energy. The surface energy is preferably less than 25 ergs per centimeter squared with its polar less than five percent of the total surface energy. In FIG. 2, a side view in cross section as taken along lines 2—2 of FIG. 1 of the preferred embodiment, the partially coated electrosurgical electrode 10 is disclosed. Note that, in FIG. 2 the cross section of the partially coated electrosurgical electrode 10 is shown enlarged and schematically so that the concept of peaks 16 and valleys 17 with the treated surface 19 forming openings 20 is readily apparent. The partial coating 18 is a fluorinated polymer making direct passage of electrosurgical energy impossible without a breakdown of the dielectric properties of the fluorinated polymer. For example, Whitford, of Westchester, Pa., Xylan 8820 has been found to work well. The fluorinated polymer may be made slightly conductive by the addition thereto of conductive matter such as powered metal or other conductor including carbon, molybdenum disulfide or mineral salts. Even so, the dielectric properties of the fluoropolymer are considered an insulator as regards the flow of electrons in the circuit 11.

The conductive sites 15 are carried on the substrate 14 and electrically couple therewith to transmit electrosurgical energy from the source 13 to and through the electrode 12. The treated surface 19 can be reduced to a relatively even level that is not entirely flat whereon the openings 20 and the filled valleys 17 of partial coating 18 form a generally undulating surface for reducing mechanical coupling of coagulum for lowering the overall surface free energy thereacross while increasing the size of the openings 20 relative to the peaks 16, as best shown in FIG. 2. The openings 20 are preferred to be in the range of about three to 20 percent of the total area of the portion of the electrically conductive electrode 10 having the conductive sites 15 preferably of the same medical grade biocompatable metallic material as the substrate 14. The treated surface 19 produces peaks 16 reduced to nearly the level of the filled valleys 17 whereby the electrode 12 is relatively smooth. The partial coating 18 thus produced has a mottled appearance of the gleaming metallic openings 20 contrasting with the coated filled valleys 17 sort of like the appearance of stars in the cloudless night sky.

The medical grade biocompatable metallic material substrate 14 is substantially an alloy of stainless steel but could be primarily a nickel chrome alloy or pure nickel. The conductive sites 15 might be formed as a plasma deposition of the same or different material as the substrate 14 wherein, for example, the substrate 14 is an iron nickel chrome alloy. A mechanically deformed surface finish on the medical grade biocompatable metallic material electrically conductive electrode 10 substrate 14 could be used to produce the peaks 16 and valleys 17 of the conductive sites 15. In particular, any pattern regular or not could be plastically formed into the substrate 14 to raise the peaks 16. A vapor deposition of the medical grade biocompatable metal or any compatible metal or alloy can form the conductive sites 15 on the medical grade biocompatable metallic material electrically conductive electrode 10 substrate 14 as the peaks 16. It may be economically desirable to have a non-medically biocompatable substrate 14 with a biocompatable conductive material for the conductive site 15. The preferred conductive material is Metec 4050C nickel chrome powder, from Metallurgical Technologies, Inc. of Pearland, Tex.

The partial coating 18 might include a solid lubricant compounded to the fluorinated polymer. Solid lubricants such as graphite, molybdenum disulfide, or the like can be compounded with the polymer. The partial coating 18 need only be any low surface energy polymer as described herein for example. The medical grade biocompatable metallic material substrate 14 or the conductive material might have a highly conductive metallic material such as an alloy with generous nickel content surface at the openings 20.

Figure 3:
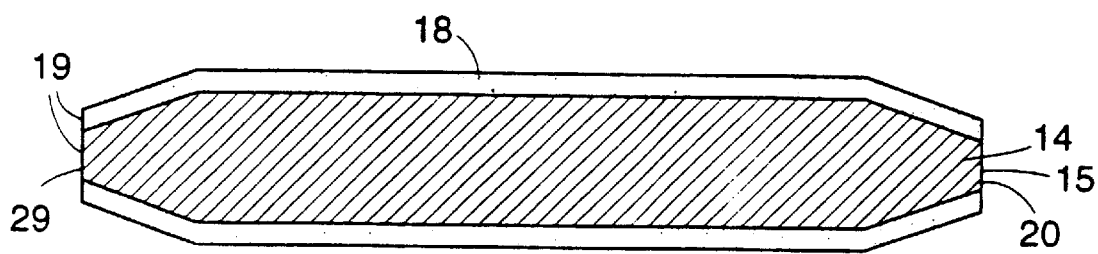
FIG. 3 is a side view in cross section as taken along lines 3—3 of FIG. 1 of an alternate embodiment of a partially coated electrosurgical electrode.

A method of manufacturing the partially coated electrosurgical electrode 10 for the application of electromagnetic energy in either the monopolar or a bipolar circuit 11 through the tissue and the bodily fluids of an animal or human includes steps. Preparing an electrically conductive electrode 10 of a medical grade metallic conductor for connection to the source 13 of electromagnetic electrosurgical energy at one end 21 thereof and for transmission of the electromagnetic electrosurgical energy in the circuit 11 from another end 22 thereof to and through the tissue and the bodily fluids of the animal or human is a step. Typically the electrosurgical electrode 12 is formed in a progressive stamping operation at high speed from 302 stainless steel sheet 0.5 mm thick. The thin stainless sheet is blanked but carried on a progression 23 shown in FIG. 4 during a multiple forming operation which produces the hollow tubular end 21 to connect with the source 13 of electrosurgical energy. The elongate paddle end 22 has thinned edges 24 as shown in FIGS. 1 and 3; the edges 24 are used by the surgeon to apply the electrosurgical energy to the tissue or bodily fluids during cutting or coagulating. Because of the openings 20, the end 22 can also be used to apply electrosurgical energy, if desired, and still be non stick and easy to clean. Different wave forms of electrosurgical energy are used for cutting or coagulating and various techniques can be applied by the surgeon to coagulate bleeding. The transfer of electrosurgical energy is by means of establishing the flow of electrons from the electrosurgical electrode 12 to the patient and then to a return in the form of a pad 25 in FIG. 1 when monopolar is used or another nearby electrode 26 when bipolar is used. Making the electrically conductive electrode 12 about its end 22 with the electrically conductive material coating that can be substantially the same as the medical grade metallic conductor has been found to work particularly well because the physical connection between the substrate 14 and the electrically conductive material coating for conductive sites 15 is excellent when the metals are the same or similar. The making of the electrically conductive electrode 12 to have peaks 16 in the range of about 1 to 50 microns in height above the valleys 17 for forming the conductive sites 15 which pass electrosurgical energy from the one end 22 of the electrically conductive electrode 12 can be another step. Applying the partial coating 18 for residing primarily in the valleys 17 and disposed to contact tissue and the bodily fluids of the animal or human during electrosurgical application of the partially coated electrosurgical electrode 10 could be a further step. Applying the partial coating 18 to a thickness in the preferred range of about 5 to 100 microns is another step. Treating surfaces 19 substantially across the peaks 16 and generally over the filled valleys 17 of the partially coated electrically conductive electrode 10 is used as a step for generating the relatively smooth non stick surface of a appropriately uniform level. The level does not have to be dead smooth or flat and so the execution is within the typical level of ordinary high speed manufacturing processes which usually leave the finished appearance under magnification with scratches, abrasions and other imperfections. The average roughness found to work acceptably is in the range of about under $R_A$ 180 micro inches. Forming openings 20 in the treated surface 19 through the partial coating 18 at the peaks 16 for exposing the electrically conductive material coating at the conductive sites 15 is another step. Locating the openings 20 primarily among the valleys 17 filled with the partial coating 18 so that the smooth treated surface 19 formed of the openings 20 and the filled valleys 17 permits the direct passage of electromagnetic electrosurgical energy through the circuit 11 between the openings 20 therein and the tissue and the bodily fluids while the filled valleys 17 provide the partial coating 18 having an easily cleaned low surface free energy is an additional step.

The step of treating the surface can be performed in many ways and several are disclosed for example but not by way of limitation. Therefore, treating the surface can be preferably performed by mass finishing including vibratory finishing the partially coated electrode 10 with abrasive material media. The preferred material media is glass or ceramic but steel or plastic can also be used. It is preferred that zirconia Z1 ceramic media with L161 deburring compound be used for treating the surface by vibratory finishing. The vibratory finishing process is typically performed for a period of time such as 15 to 90 minutes and is accomplished in a container that carries and rotates so the plurality of electrosurgical electrodes are tossed against one another, the media or the container. The step of treating could be performed by tumbling a plurality of the partially coated electrodes together with or without the media. The surface finish on mass finished electrodes is thus generally uniform. The step of treating is performed by polishing or buffing the partially coated electrode 10 with abrasive material, e.g. aluminum oxide. The polishing or buffing operation can be performed while the electrodes are carried on the progression 23 during or after the stamping operations. The step of treating is alternatively performed by buffing the partially coated electrode 10 with abrasive material before, during or after the progressive stamping operation. The step of treating could be performed by abrasive belt grinding or sanding the partially coated electrode 10 with abrasive material. The step of treating might be performed by surface grinding the partially coated electrode with abrasive material. The step of treating might be performed by burnishing using rollers or through a die.

Similarly, the step of making the peaks 16 and valleys 17 can be accomplished is a variety of ways and the possibilities herein are but a few examples presented to disclose the sort of method steps potentially available. The step of making can be performed by stamping the one end 22. The step of making may be performed by coining the one end 22. The step of making could be performed by burnishing the one end 22. The step of making might be performed by embossing the one end 22. The step of making can be performed by threading the one end 22. The step of making may be performed by knurling the one end 22. The step of making is performed by etching the one end 22. The step of making could be performed by shot peening the one end 22. The step of making might be performed by wire brushing the one end 22. The step of making can be performed by grit blasting the one end 22. The step of making can be performed by high velocity oxygen fuel spraying the one end 22 with powder, e.g. any metallic or conductive material can be used. The step of making is in another method performed by electric arc spraying the one end 22 with a conductive wire material. The step of making may be performed by high velocity oxygen fuel spraying the one end 22 with a conductive material. The preferred step of making is performed by plasma spraying the one end 22 with a conductive material.

A method of manufacturing the partially coated electrosurgical electrode 10 has steps including coating a portion 27 of a strip 28 of medical grade sheet metal with a low surface energy polymer and forming electrosurgical electrodes 12 in a progressive stamping operation including severing through the coated portion 27 to produce at least a raw conductive edge 29 for electrosurgery, see for example FIGS. 3 and 4. FIG. 3 is an enlarged cross section taken transversely to the longer dimension of the electrosurgical electrode 12. The step of coating the portion 27 of the electrosurgical electrode 12 with conductive material having peaks and valleys prior to the step of coating the portion 27, although this is not specifically shown. In FIG. 3 the concept is exactly that described for FIG. 2. The step of making can be by plasma deposition.

What is claimed is:

1. A partially coated electrosurgical electrode for the application of electromagnetic energy in either a monopolar or a bipolar circuit through the tissue and the bodily fluids of an animal or human comprising:

an electrically conductive electrode for connection to a source of electromagnetic electrosurgical energy and for transmission of the electromagnetic electrosurgical energy in the circuit to and through the tissue and the bodily fluids of the animal or human;

a portion of the electrically conductive electrode having a medical grade biocompatible metallic material as a substrate thereof, the portion located for the application of electromagnetic energy in either a monopolar or a bipolar circuit to and through the tissue and the bodily fluids of an animal or human;

conductive sites for passing electrosurgical energy, the conductive sites located on and in uninterrupted contact with the portion of the medical grade biocompatible metallic material substrate, the conductive sites including peaks and valleys and formed of conductive material, wherein the conductive sites on the substrate transmits energy in the form of electrons and wherein the medical grade biocompatible metallic material substrate is substantially an electric arc sprayed deposition of an alloy of stainless steel;

a partial coating residing primarily in the valleys disposed for contact with the tissue and the bodily fluids of the animal or human during electrosurgical application of the partially coated electrosurgical electrode, the partial coating having a low surface free energy, wherein the partial coating is a fluorinated polymer and includes a compounded solid lubricant;

a treated surface substantially across the peaks and generally over the filled valleys of the partially coated electrically conductive electrode, the treated surface being relatively smooth for non stick characteristics during application of electrosurgical effects to tissue and bodily fluids, and openings in the treated surface through the partial coating, the openings formed in the treated surface at the peaks exposing the conductive material of the conductive sites, the openings located primarily among the valleys filled with the partial coating, wherein the treated surface is reduced to a level so the openings and the filled valleys of the partial coating form a generally smooth surface for reducing mechanical coupling of coagulum and lowering the surface free energy thereacross.

2. A partially coated electrosurgical electrode for the application of electromagnetic energy in an electrosurgical circuit, the partially coated electrode comprising:

an electrically conductive electrode adapted for connection to a source of electromagnetic electrosurgical energy and for transmission of the electromagnetic electrosurgical energy in the circuit;

a portion of the electrically conductive electrode having a medical grade biocompatible metallic material, the portion located for the application of electromagnetic energy in the circuit;

conductive sites for passing electrosurgical energy, the conductive sites located on and in uninterrupted contact with the portion of the medical grade biocompatible metallic material, the conductive sites formed of conductive material;

a partial polymer coating disposed on the conductive sites for use in electrosurgical application of the partially coated electrosurgical electrode, the partial coating having a low surface free energy, and openings through the partial coating, the openings exposing the conductive sites, the openings and the partial polymer coating forming a generally undulating surface.

3. The partially coated electrosurgical electrode of claim 2 wherein the polymer coating is compounded with a solid lubricant.

4. The partially coated electrosurgical electrode of claim 3 wherein the solid lubricant is graphite.

5. The partially coated electrosurgical electrode of claim 3 wherein the solid lubricant is molybdenum disulfide.

6. A partially coated electrosurgical electrode for cutting and coagulating tissue, the electrode comprising:

a substrate;

a stratum disposed in uninterrupted contact with the substrate and in electrical communication therewith; and a partial coating disposed on the stratum, the partial coating defining openings exposing the stratum.

7. A partially coated electrosurgical electrode according to claim 6, wherein the partial coating is a fluorinated polymer including a solid lubricant.

8. A partially coated electrosurgical electrode according to claim 6, further including a treated surface disposed on the partial coating.

9. A partially coated electrosurgical electrode according to claim 6, wherein the stratum includes a portion configured as peaks and valleys.

\* \* \* \* \*